(12) United States Patent
Braguti et al.

(10) Patent No.: US 11,389,496 B2
(45) Date of Patent: Jul. 19, 2022

(54) ANTIFUNGAL COMPOSITIONS

(71) Applicant: BIOKOSMES SRL, Milan (IT)

(72) Inventors: Lodovico Braguti, Bosisio Parini (IT);
Jeremy Anthony Philip Randall,
Bosisio Parini (IT)

(73) Assignee: BIOKOSMES SRL, Milan (IT)

( * ) Notice: Subject to any disclaimer, the term of this patent is extended or adjusted under 35 U.S.C. 154(b) by 170 days.

(21) Appl. No.: 16/629,975

(22) PCT Filed: Jul. 10, 2018

(86) PCT No.: PCT/IB2018/055061
§ 371 (c)(1),
(2) Date: Jan. 10, 2020

(87) PCT Pub. No.: WO2019/012412
PCT Pub. Date: Jan. 17, 2019

(65) Prior Publication Data
US 2020/0129577 A1     Apr. 30, 2020

(30) Foreign Application Priority Data

Jul. 11, 2017   (IT) .................. 102017000078091

(51) Int. Cl.
| | |
|---|---|
| *A61K 36/53* | (2006.01) |
| *A61P 17/12* | (2006.01) |
| *A61K 9/00* | (2006.01) |
| *A61K 31/047* | (2006.01) |
| *A61K 31/17* | (2006.01) |

(Continued)

(52) U.S. Cl.
CPC ............ *A61K 36/53* (2013.01); *A61K 9/0014* (2013.01); *A61K 31/047* (2013.01); *A61K 31/17* (2013.01); *A61K 31/19* (2013.01); *A61K 47/34* (2013.01); *A61P 17/12* (2018.01)

(58) Field of Classification Search
None
See application file for complete search history.

(56) References Cited

U.S. PATENT DOCUMENTS

| | | | |
|---|---|---|---|
| 5,939,085 A | 8/1999 | Jacobs et al. | |
| 6,846,837 B2 * | 1/2005 | Maibach ............ | A61K 31/4965 514/350 |

(Continued)

FOREIGN PATENT DOCUMENTS

| | | | |
|---|---|---|---|
| CN | 103535385 | * | 1/2014 |
| CN | 103535385 A | | 1/2014 |

OTHER PUBLICATIONS

Search Report and Written Opinion of PCT/IB2018/055061 dated Oct. 8, 2018.

*Primary Examiner* — Melissa S Mercier
(74) *Attorney, Agent, or Firm* — Silvia Salvadori, P.C.; Silvia Salvadori

(57) ABSTRACT

Disclosed are compositions/formulations for topical use designed for the treatment of fungal infections of the nails, comprising antifungal compounds combined with keratolytic agents and with one or more cationic polymers having an adhesive activity towards the keratins of the nails. The compositions/formulations form a physical barrier on the surface of the keratin tissues which guarantees long-term adherence of the antifungal compounds to the keratin surface, providing a high gradient of concentration for penetration, and greater efficacy.

3 Claims, 1 Drawing Sheet

(51) Int. Cl.
*A61K 31/19* (2006.01)
*A61K 47/34* (2017.01)

(56) References Cited

U.S. PATENT DOCUMENTS

| | | | |
|---|---|---|---|
| 8,672,274 B2 * | 3/2014 | Albisua Aspiazu | ...... B61L 5/10 |
| | | | 246/468 |
| 2010/0215775 A1 | 8/2010 | Schmaus et al. | |
| 2015/0265666 A1 | 9/2015 | Modak et al. | |
| 2016/0100574 A1 | 4/2016 | Pesaro et al. | |

* cited by examiner

ANTIFUNGAL COMPOSITIONS

This application is a U.S. national stage of PCT/IB2018/055061 filed on 10 Jul. 2018, which claims priority to and the benefit of Italian Application No. 102017000078091 filed on 11 Jul. 2017, the contents of which are incorporated herein by reference in their entireties.

FIELD OF INVENTION

The present invention relates to compositions for topical use for the treatment of fungal infections of the nails, comprising essential oil of *Thymus vulgaris*, 1,2-decanediol, keratolytic agents and a cationic polymer with adhesive activity towards the keratins of the nails and skin.

The combination consisting of *Thymus vulgaris* essential oil and 1,2-decanediol exhibits a considerable, unexpected, synergic antifungal effect.

The cationic polymer forms a physical barrier on the surface of the keratin tissues which guarantees long-term adherence of the antifungal compounds to the surface of the keratin, providing a high gradient of concentration for penetration, and greater efficacy.

BACKGROUND TO THE INVENTION

Onychomycosis is a nail infection caused by dermatophyte fungi, yeasts or moulds. Fungal infections of the nails give rise to functional and aesthetic problems for patients, causing difficulties in their personal and working lives (Wollina U et al., Deutsch Arztbl Int. 2016 Jul. 25; 113(29-30):509-18.).

Onychomycosis is widespread all over the world (Sang-Ha Kim et al., Osong Public Health Res Perspect 2015 6(6), 341e345). In Europe and the USA its epidemiological incidence is 4.3%, with a higher incidence among the hospitalised population, namely 8.9%. The incidence increases with age, and is highest among people aged over 65. The pathogen that most commonly causes onychomycosis is *Trichophyton rubrum*, a dermatophyte fungus found in about 65% of cases. Moulds are found in 13.3% of cases, and yeasts in 21.1%.

Recently, pathogenic yeasts have been diagnosed increasingly often as being responsible for onychomycosis. For example, *Candida albicans* gives rise to chronic candidiasis, which involves the entire nail apparatus.

Non-dermatophyte fungi are also diagnosed increasingly often as being responsible for onychomycosis. For example, *Scopulariopsis* spp. causes onychomycosis of the toenail.

Fungal infections can be transmitted between family members, by one spouse to the other or by parents to children. The predisposing factors to onychomycosis include nail trauma, advanced age, and vascular disease.

The treatment of onychomycosis usually takes several months. Recurrences can take place a year or more after the infection was eradicated, are very common, and can affect over half of all successfully treated patients. A recurrence/reinfection percentage of 20-25% is cited in the literature, with recurrence rates ranging from 6.5 to 53%.

Topical treatment is highly desirable in view of its localised effects, as it gives rise to minimal systemic adverse events and can improve compliance with the treatment.

The topical treatments currently used are mainly designed for: (1) mild or moderate stages of the disease, (2) in combination with other systemic agents, (3) for the prevention of recurrences, (4) in cases where patients are not good candidates for oral antifungal treatment (Tosti A. Elewski B E., Skin Appendage Disord., 2016 September; 2(1-2):83-87. Epub 2016 Sep. 14; Faergemann J, Swanbeck G., Mycoses, 1989 October; 32(10):536).

Topical agents, in order to be effective, must penetrate and accumulate in the nailbed. However, the keratinised structure of the nail presents high resistance to permeation by antifungal agents (Fernandez-Flores A. et al, Rom J Morphol Embryol. 2014; 55(2):235-56).

Antifungal and antibacterial compositions comprising thyme essential oil or thymol, a terpene which is the main component of thyme oil, are disclosed in US 2009028119, U.S. Pat. No. 8,945,596 and US 20060073218. The antifungal activity of thyme essential oil and the terpenes it contains is also described in Ramsewak R S et al., Phytother Res. 2003 April; 17(4):376-9, Flores F. C., Mycopathologia, February 2016, Volume 181, 1, pp 9-15 and Fontenelle R O. et al., Molecules. 2011 Jul. 29; 16(8):6422-31.

1,2-Decanediol has antimicrobial activity against the micro-organisms responsible for skin mycoses and onychomycoses such as Tricophytum, Epidermophyton and *Candida albicans*, with very low Minimum Inhibitory Concentrations (R. Pillai et al., Cosmetics Toiletries Journal, vol. 123, pp. 53-64, 2008; N. Togashi et al., Molecules, vol. 12, no. 2, pp. 139-148, 2007; Schmaus G. et al., IFSCC Congress; Barcelona 2008).

Topical antibacterial compositions comprising 1,2-decanediol are described in U.S. Pat. Nos. 4,294,728 and 9,511,040.

DESCRIPTION OF THE INVENTION

Figure 1:
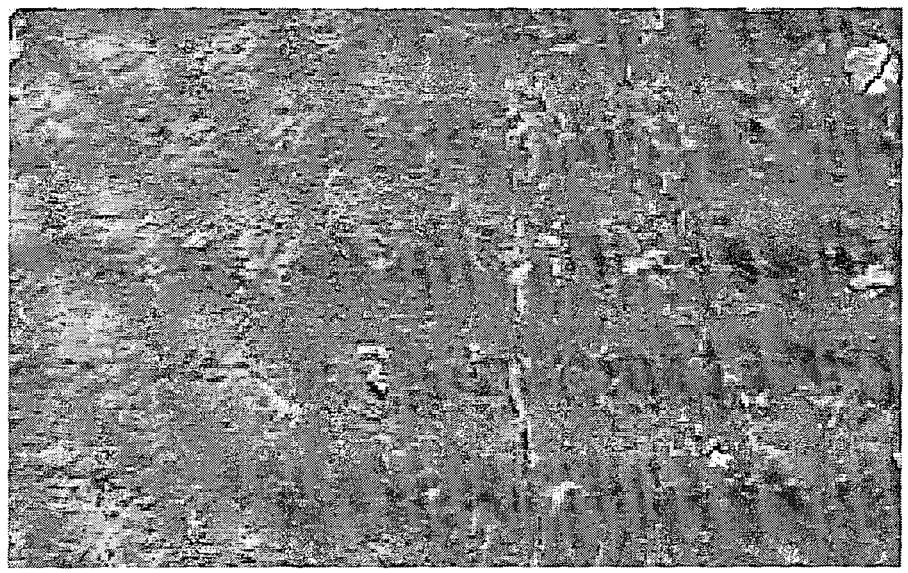
FIG. 1 shows the untreated nails.

It has now been found that the combined use in a single formulation of:

1. A combination of specific antimicrobial substances (active against the yeasts and moulds responsible for onychomycosis)
2. A keratolytic system that promotes transungual absorption of the specific associative antimicrobial system
3. An adhesive cationic polymer that provides the antimicrobial and keratolytic combination with a lengthy residence time gives rise to a synergic action in the topical treatment of onychomycosis.

The combination according to the invention comprises in particular:

a) a synergic combination of antifungal agents consisting of a 1,2-alkanediol, preferably 1,2-decanediol, and *Thymus vulgaris* essential oil;

b) at least one keratolytic agent that promotes absorption and transungual permeation of the specific antimicrobial system and c) a cationic adhesive polymer.

The effectiveness of the formulation of the invention in treating the pathogenic yeasts and pathogenic fungi mainly responsible for onychomycosis is unexpected, and greater than that obtained with the antifungal system alone or the single keratolytic system, due to the synergic action of the three compounds and the increased residence time of the formulation.

According to the invention, quaternary polymers that carry positive electrical charges are selected, thus neutralising the negative charges (and therefore reducing the surface static electricity). Examples of preferred polymers include polyquaternium-7, behentrimonium chloride, behentrimonium methosulphate, cetrimonium chloride, stearalkonium chloride, guar hydroxypropyltrimonium chloride, hydroxypropyl guar hydroxypropyltrimonium chloride, dipalmitoylethyl hydroxyethylmonium methosulphate, dihydrogenated palmoylethyl hydroxyethylmonium methosulphate, distearoylethyl hydroxyethylmonium methosulphate, dicocoylethyl hydroxyethylmonium methosulphate, hydroxyethyl dimonium chloride, cocodimonium hydroxypropyl hydrolysed wheat protein, lauryl methyl gluceth-10 hydroxypropyldimonium chloride, silicone quaternium-17, silicone quaternium-22, trimethylsiloxysilicate, C11-15 pareth-5, C11-15 pareth-9, phenyltrimethicone and quaternised proteins or honey.

Polyquaternium-7, a cationic polymer obtained by polymerisation of acrylamide with dimethyl diallylammonium chloride, is particularly preferred. Polyquaternium-7 is used as an antistatic, film-forming and fixative agent in a wide range of cosmetics, especially hair-care products, due to its affinity with keratin, which is attributable to the electrostatic interactions between sites with opposite charges on the keratin and the polymer. The polymer therefore continues to adhere to the surface of the keratin, creating a long-lasting protective film.

*Thymus vulgaris* essential oil is particularly indicated for topical treatment of onychomycosis because it possesses proven efficacy, a low likelihood of development of resistant species, and a low rate of side effects. The main ingredients of the essential oil are low-molecular-weight terpenes that easily penetrate the nailplate until they reach the fungi responsible for the infection. Thymol, the main terpene in thyme essential oil, is a natural remedy effective against the pathogenic micro-organisms responsible for skin and nail mycosis.

The combination of *Thymus vulgaris* essential oil and 1,2-decanediol of the invention exerts synergic effects against fungi, combined with the keratolytic and film-forming activity of quaternary polymers.

*Thymus vulgaris* essential oil is present in the compositions of the invention in concentrations preferably ranging from 0.1% to 5% (w/w), while 1,2-decanediol is preferably present in concentrations ranging from 0.1% to 5% (w/w).

The concentration of the adhesive cationic polymer(s), in particular polyquaternium-7, preferably ranges from 0.1% to 5% (w/w).

Examples of keratolytic agents include lactic acid, glycolic acid, mandelic acid, salicylic acid and derivatives thereof, lactobionic acid and derivatives thereof, gluconolactone and derivatives thereof, and mixtures of lactic acid and urea, preferably mixtures of lactic acid and urea in concentrations ranging from 30 to 50% (w/w) with a urea-lactic acid weight ratio ranging from 0.5:1 to 1:0.5.

The formulations can also contain suitable carriers or excipients such as surfactants, solvents, preservatives, perfumes and pH regulators.

The compositions of the invention can take the form of a serum, gel, oil, aqueous solution, water-alcohol solution or nail varnish.

The compositions of the invention are useful in the topical treatment of fungal onychomycosis, even when it is resistant to other antifungals.

The compositions of the invention form a film on the surface of the keratin tissues of the nails which constitutes a physical barrier on the surface and guarantees long-term adherence of the antifungal compounds to the keratin surface, thus promoting better penetration and an unexpected synergic antifungal effect.

The invention is illustrated in detail in the following examples.

Examples 1-5 Formulations

| | code | | | | |
|---|---|---|---|---|---|
| Ingredient | Formulation 1 | Formulation 2 | Formulation 3 | Formulation 4 | Formulation 5 |
| WATER | Qs to 100 g | Qs to 100 g | Qs to 100 g | Qs to 100 g | Qs to 100 g |
| POLYQUATERNIUM-7 | 0.5 g | 0.5 g | 0.5 g | 2 g | 0.5 g |
| 80% LACTIC ACID | 16.25 g | 16 g | 16 g | 15 g | 20 g |
| SODIUM HYDROXIDE DROPS | 0.325 g | 0.325 g | 0.325 g | 0.325 g | 0.325 g |
| ETHYL ALCOHOL | 35 g | 35 g | 35 g | 35 g | 35 g |
| UREA | 20 g | 20 g | 18 g | 20 g | 16 g |
| ETHOXYDIGLYCOL | 2.5 g | 2.5 g | 2.5 g | 2.5 g | 2.5 g |
| COPPER USNATE | 0.2 g | 0.2 g | 0.2 g | 0.2 g | 0.2 g |
| 1-2 DECANEDIOL | 1 g | 1 g | 0.2 g | 1 g | 1 g |
| *THYMUS VULGARIS* ESSENTIAL OIL | 0.2 g | 0.2 g | 1 g | 0.2 g | 0.3 g |

Example 6: Evaluation of Minimum Inhibitory Concentration (MIC) Against Fungi

The MIC of the following compositions against *Candida albicans* was evaluated:

| Ingredient | Placebo | Comparative example 1 0BIO4B010 PON/E | Comparative example 2 0BIO4B010 PON/B | Comparative example 3 0BIO4B010 PON/D | Example 4 0BIO4B010 PON |
|---|---|---|---|---|---|
| WATER | Qs to 100 g | Qs to 100 g | Qs to 100 g | Qs to 100 g | Qs to 100 g |
| POLYQUATERNIUM-7 | 0.5 g | 0.5 g | 0.5 g | 0.5 g | 0.5 g |
| 80% LACTIC ACID | / | 16.25 g | 16.25 g | 16.25 g | 16.25 g |
| SODIUM HYDROXIDE DROPS | / | 0.325 g | 0.325 g | 0.325 g | 0.325 g |
| ETHYL ALCOHOL | | 35 g | 35 g | 35 g | 35 g |
| UREA | | 20 g | 20 g | 20 g | 20 g |
| ETHOXYDIGLYCOL | | 2.5 g | 2.5 g | 2.5 g | 2.5 g |
| COPPER USNATE | 0.2 g | 0.2 g | 0.2 g | 0.2 g | 0.2 g |
| 1-2 DECANEDIOL | / | / | 1 g | / | 1 g |
| THYMUS VULGARIS ESSENTIAL OIL | / | / | / | 0.2 g | 0.2 g |
| MIC *Candida albicans* | >50% | >5 < 6% | >3 < 4% | >3 < 4% | >1 < 2% |

(0BIO4B010PON), composition containing both antifungal ingredients (1,2-decanediol and *Thymus vulgaris* essential oil) combined with the urea-lactic acid keratolytic system (example 4).
 (0BIO4B010PON/E): composition containing the urea-lactic acid keratolytic combination only.
 (0BIO4B010PON/B): composition containing 1,2-decanediol and the urea-lactic acid keratolytic system only.
 (0BIO4B010PON/D): composition containing *Thymus vulgaris* essential oil and the urea-lactic acid keratolytic system only.
 Placebo: composition without antifungal ingredients (1,2-decanediol and
 *Thymus vulgaris* essential oil) and without the urea-lactic acid keratolytic system.

For each composition, a set of 10 sterile tubes is prepared in duplicate.

Scalar volumes of the solution of the composition to be tested and of the TSB (Tryptone Soy Broth) volumes are added to each sterile tube until a total volume of 9.90 ml is reached. After mixing, aliquots of 100 μl of the specific microbial suspension containing 107 CFU/ml are added to each set. The tube contents are mixed with a vortex, and the tubes are incubated at 37° C.+1° C. for 24 hours.

A negative control is also prepared for each composition to be tested, consisting of a sterile tube containing the highest concentration of the test product and of the culture medium.

A positive control is also prepared for the micro-organism, consisting of a sterile tube containing 100 μl aliquots of the microbial suspension containing 107 CFU/ml and 9.90 ml of the appropriate broth.

The MIC is determined by evaluating microbial growth, which causes cloudiness of the medium.

The pair of tubes containing the minimum dilution of the product wherein no visible microbial growth is detectable (the solution is not cloudy) represents the MIC of the product for the micro-organism tested.

The MIC was evaluated on the values obtained in 2 experiments.
 (0BIO4B010PON): composition containing both antifungal ingredients (1,2-decanediol and *Thymus vulgaris* essential oil) combined with the urea-lactic acid keratolytic system, which presents a MIC>1<2%),
 (0BIO4B010PON/E): composition containing the urea-lactic acid keratolytic combination only, which presents a MIC>5%-<6%,
 (0BIO4B010PON/B): composition containing 1,2-decanediol and the urea-lactic acid keratolytic system only, which presents a MIC>3%-<4%,
 (0BIO4B010PON/D): composition containing *Thymus vulgaris* essential oil and the urea-lactic acid keratolytic system only, which presents a MIC>3%-<4%,
 Placebo: presents a MIC>50%.

The results demonstrate that the composition containing the antifungal system 1,2-decanediol and *Thymus vulgaris* essential oil combined with the urea-lactic acid keratolytic system and polyquaternium-7 exercised a surprising effect compared with the placebo system alone and with the single antifungal and keratolytic systems.

The composition of the invention (0BIO4B010PON) was also evaluated and confirmed against *Trichophyton rubrum* ATCC 28188 and *Scopulariopsis acremonium* ATCC 58636, the fungi primarily responsible for fungal infections of the skin and nails; the MIC against *Trichophyton rubrum* ATCC 28188 is >0.5%-<1%, while the MIC against *Scopulariopsis acremonium* ATCC 58636 is >1%-<2%.

The results demonstrate a high level of broad-spectrum antifungal activity. This confirms the innovative, synergic activity of the combination of the three systems (antibacterial, keratolytic and polymer).

The film-forming activity of the following invention was verified with an in vitro SEM test, which analysed the surface of the nail matrix concerned, treated with formula (0BIO4B010PON) or untreated.

Example 7: In Vitro Test to Establish the Ability of the Composition to Create a Superficial Adhesive Barrier on the Nail Surface: Scanning Electron Microscope (SEM) Analysis of the Treated Nail The non-treated nail (NT) was coated with a layer of gold to take the photomicrographs; the treated nail (T) was coated with a double layer of the composition of the invention and dried at room temperature for 1 day or stove-dried at 50° C.; both samples were then coated with a layer of gold to take the photomicrographs.

Figures 2, 3:
FIG. 2 shows the product dried at 50° C.
FIG. 3 shows the product dried at room temperature.

The results are shown in FIGS. 1-3: FIG. 1 shows the untreated nails, FIG. 2 the product dried at 50° C., and FIG. 3 the product dried at room temperature.

The microanalysis conducted on the portion of nail illustrated above indicates the percentage atomic composition set out in the table below.

| ELEMENT | % ATOMIC COMPOSITION BEFORE | % ATOMIC COMPOSITION AFTER |
|---|---|---|
| Carbon | 62.10 | 66.84 |
| Oxygen | 36.68 | 32.04 |
| Sodium | 0.22 | 0.20 |
| Silicon | 0.14 | 0.06 |
| Sulphur | 0.66 | 0.22 |
| Chlorine | 0.07 | 0.0 |
| Potassium | 0.05 | 0.0 |
| Calcium | 0.08 | 0.64 |

The comparison (before and after treatment) demonstrates that the surface composition of the nail significantly changed after treatment. After treatment, the percentages of carbon and calcium increased, whereas the concentrations of sulphur and silicon (typical of the nail composition) declined. The photomicrographs shown demonstrate that the nail is coated with the product, because the electron beam penetrates the material to a depth of about 1 micron. It can therefore be concluded that the thickness of the product applied is about 1 micron, and that the small amounts of sulphur and silicon found, partly detected by the electron microscope, are due to the composition of the underlying nail.

The invention claimed is:

1. A method of treating onychomycosis with cosmetic or dermatological compositions or medical devices, said cosmetic or dermatologic compositions or medical devices comprising:
   a) a synergic combination of antifungal agents consisting of from 0.1% to 5% (w/w) 1,2-decanediol and from 0.1% to 5% (w/w) *Thymus vulgaris* essential oil;
   b) at least one keratolytic agent, wherein the keratolytic agent consists of a mixture of urea and lactic acid; and
   c) an adhesive cationic polymer, wherein the adhesive cationic polymer is polyquaternium-7 in concentrations from 0.1% to 5% (w/w).

2. The method according to claim 1, wherein the concentration of the mixture of urea and lactic acid ranges from 30 to 50%, and the urea-lactic acid weight ratio ranges from 0.5:1 to 1:0.5.

3. The method according to claim 1, in the form of a serum, gel, aqueous solution, water-alcohol solution or nail varnish.

* * * * *

UNITED STATES PATENT AND TRADEMARK OFFICE
CERTIFICATE OF CORRECTION

| | | |
|---|---|---|
| PATENT NO. | : 11,389,496 B2 | |
| APPLICATION NO. | : 16/629975 | |
| DATED | : July 19, 2022 | |
| INVENTOR(S) | : Lodovico Braguti and Jeremy Anthony Philip Randall | |

It is certified that error appears in the above-identified patent and that said Letters Patent is hereby corrected as shown below:

On the Title Page

Item (54) and in the Specification, Column 1, Line 1:
-- ANTIFUNGAL COMPOSITIONS --
Should read:
"NOVEL ANTIFUNGAL COMPOSITIONS"

Signed and Sealed this
Seventeenth Day of January, 2023

Katherine Kelly Vidal
*Director of the United States Patent and Trademark Office*